United States Patent
Iyer et al.

(10) Patent No.: US 9,133,076 B2
(45) Date of Patent: Sep. 15, 2015

(54) INTEGRATED CARBON CAPTURE AND GAS TO LIQUIDS SYSTEM

(71) Applicant: Linc Energy Ltd, Brisbane, Queensland (AU)

(72) Inventors: Raj Iyer, Monroe Township, NJ (US); Bipin Patel, Richmond, TX (US)

(73) Assignee: Linc Energy Ltd, Brisbane, Queensland (AU)

( * ) Notice: Subject to any disclaimer, the term of this patent is extended or adjusted under 35 U.S.C. 154(b) by 0 days.

(21) Appl. No.: 14/404,872

(22) PCT Filed: Jun. 4, 2013

(86) PCT No.: PCT/AU2013/000586
§ 371 (c)(1),
(2) Date: Dec. 1, 2014

(87) PCT Pub. No.: WO2013/181693
PCT Pub. Date: Dec. 12, 2013

(65) Prior Publication Data
US 2015/0126625 A1    May 7, 2015

Related U.S. Application Data

(60) Provisional application No. 61/655,774, filed on Jun. 5, 2012.

(51) Int. Cl.
*C07C 27/00* (2006.01)
*C07C 1/12* (2006.01)
*C01B 3/00* (2006.01)
*C10G 2/00* (2006.01)
*C07C 1/04* (2006.01)

(52) U.S. Cl.
CPC ... *C07C 1/12* (2013.01); *C01B 3/00* (2013.01); *C07C 1/04* (2013.01); *C10G 2/00* (2013.01)

(58) Field of Classification Search
CPC ............. C07C 1/04; C10G 2/00; C01B 3/00; C01B 2203/0805
USPC ........................................................ 518/700
See application file for complete search history.

(56) References Cited

U.S. PATENT DOCUMENTS

| 6,784,329 B2 | 8/2004 | O'Rear et al. | |
| 8,414,689 B2 * | 4/2013 | Tirio | ................................. 95/96 |
| 2011/0088550 A1 | 4/2011 | Tirio | |

FOREIGN PATENT DOCUMENTS

EP    0516441 B2    4/2009

OTHER PUBLICATIONS

International Search Report of the International Searching Authority, mailed Aug. 20, 2013, for corresponding International Application No. PCT/AU2013/000586, 4 pages.

* cited by examiner

*Primary Examiner* — Sudhakar Katakam
(74) *Attorney, Agent, or Firm* — Klarquist Sparkman, LLP

(57) ABSTRACT

A gas to liquids process is described wherein carbon dioxide is captured and used within the gas to liquids process.

12 Claims, 2 Drawing Sheets

INTEGRATED CARBON CAPTURE AND GAS TO LIQUIDS SYSTEM

CROSS REFERENCE TO RELATED APPLICATIONS

This is the U.S. National Stage of International Application No. PCT/AU2013/000586, filed Jun. 4, 2013, which in turn claims the benefit of U.S. Provisional Application No. 61/655,774, filed Jun. 5, 2012.

TECHNICAL FIELD

The present disclosure relates gas to liquids systems, and specifically to gas to liquids processes that can be used in and/or integrated with refinery and petrochemical facilities.

BACKGROUND ART

Gas to liquid (GTL) processes can be used to convert gaseous hydrocarbons, such as natural gas, into higher molecular weight hydrocarbon materials, such as gasoline and/or diesel. Conventional GTL processes can convert methane rich gases into various liquid fuels through direct chemical conversion or through an intermediate syngas. There are multiple processes known in the art, such as, for example, the Fischer-Tropsch (FT) process and the Mobil "methanol to gasoline" (MTG) process. The Fischer-Tropsch process encompasses the partial oxidation or reforming of methane to carbon dioxide, carbon monoxide, hydrogen, and water. The water gas shift reaction can be used to control or adjust the ratio of carbon monoxide to hydrogen in the system. In the Mobil process, methane is converted to syngas, which is subsequently converted to methanol and then polymerized to produce various alkanes and other hydrocarbon liquids.

In conventional gas to liquid processes, carbon dioxide is either vented to the atmosphere or captured and subsequently sequestered, for example, in subterranean formations. Venting carbon dioxide to the atmosphere can create environmental concerns, and the capture and sequestration of carbon dioxide can be expensive. Accordingly, there is a need to address process design issues in traditional gas to liquids processes. These needs and other needs are satisfied by the compositions and methods of the present disclosure.

SUMMARY OF INVENTION

In accordance with the purpose(s) of the invention, as embodied and broadly described herein, this disclosure, in one aspect, relates to gas to liquids processes and methods for producing hydrocarbon materials therefrom. According to aspects of the disclosed invention and as described in more detail below, a gas to liquids processes can be integrated with conventional carbon capture process in an existing cracker facility, such that the carbon dioxide captured from any one or more flue gas stream of the cracker facility can in turn be used as reaction media for reforming hydrocarbons, such as natural gas or natural gas liquids to Fischer Tropsch synthesis gas. In still further aspects, a carbon dioxide capture plant can be powered at least in part with by-product energy resulting from a Fischer Tropsch synthesis process.

Among several advantages and benefits that will be appreciated by one of ordinary skill in the art, the disclosed integrated process can ultimately reduce and assist with the control of certain regulated emissions, including for example carbon dioxide, and the so-called SOx and NOx gases. Additionally, the energy integration between the carbon capture unit and the GTL process, as summarized above, can minimize an energy (power/steam) plant's loss of capacity resulting from integrating the $CO_2$ capture process with power/steam production and thus can help maintain the total revenue of an integrated petrochemical complex.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF DRAWINGS

The accompanying figures, which are incorporated in and constitute a part of this specification, illustrate several aspects and together with the description serve to explain the principles of the invention.

DESCRIPTION OF EMBODIMENTS

Figure 1:
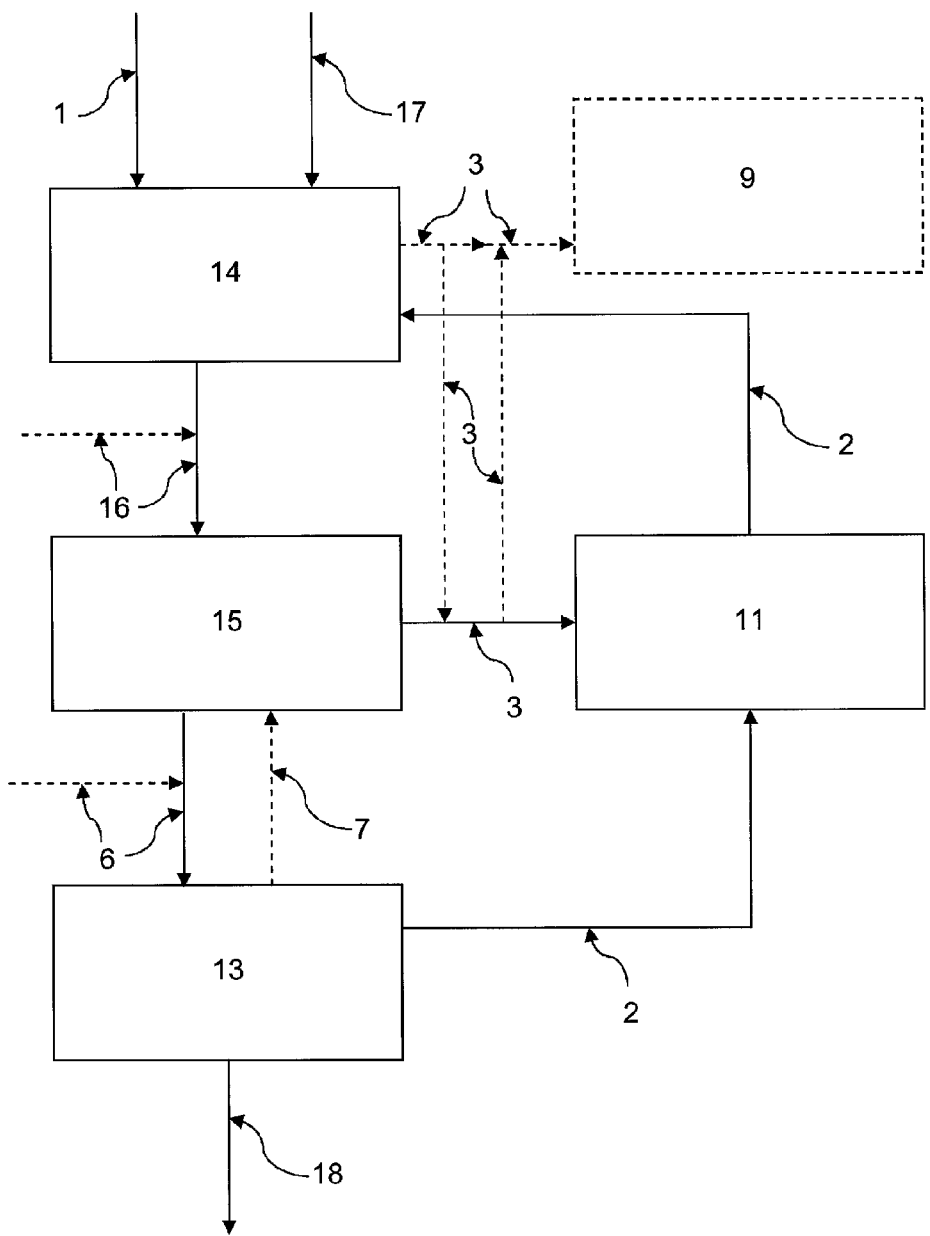
FIG. 1 is an exemplary schematic of an inventive integrated gas to liquids (GTL) process and carbon capture process in accordance with various aspects of the present disclosure.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a," "an" and "the" include plural referents unless the context clearly dictates otherwise. Thus, for example, reference to "carbon dioxide stream" includes two or more such carbon dioxide streams, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

Throughout this specification, unless the context requires otherwise, the word "comprise," or variations such as "comprises" or "comprising," will be understood to include a stated integer or step or group of integers or steps but not exclude any other integer or step or group of integers or steps.

Disclosed are various processes and system components to be used to prepare the inventive systems of the invention. It is understood that when combinations, subsets, interactions, groups, etc. of these processes and components are disclosed that while specific reference of each various individual and collective combinations and permutation of these systems cannot be explicitly disclosed, each is specifically contemplated and described herein. For example, if a particular process configuration is disclosed and discussed and a number of modifications can be made, such as various sources of captured carbon dioxide, specifically contemplated is each and every combination and permutation of the process or system and the various modifications that are possible unless specifically indicated to the contrary. This concept applies to all aspects of this application. It is understood that the compositions disclosed herein have certain functions. Disclosed herein are certain structural requirements for performing the disclosed functions and it is understood that there are a variety of structures that can perform the same function that are related to the disclosed structures, and that these structures will typically achieve the same result.

As used herein, unless specifically stated to the contrary, the term "natural gas" is intended to refer to subsurface gas and/or gas obtained from a subsurface environment, that can be in association with a crude oil or not associated with a crude oil, wherein the gas comprises methane as a major component, and optionally other hydrocarbons and/or non-hydrocarbons, such as, for example, nitrogen, carbon dioxide, and/or sulfur containing compounds.

As used herein, unless specifically stated to the contrary, the terms "synthesis gas" or "syngas" are intended to refer to a gas mixture comprising carbon monoxide and hydrogen. In a further aspect, the syngas can further comprise $CO_2$. In another aspect, the syngas can further comprise methane. In this context, syngas produced from a methane-rich source (e.g., through reforming of natural gas) can comprise primarily carbon monoxide, hydrogen, and to a lesser extent, carbon dioxide, and to a lesser extent residual methane.

As used herein, unless specifically stated to the contrary, the terms "Fischer-Tropsch process", "FT process", "Fischer-Tropsch synthesis", and "FT synthesis" are intended to refer to one or more chemical reactions used in the conversion of carbon monoxide and hydrogen into liquid hydrocarbons. In this context, a "Fischer-Tropsch synthesis unit" would refer to a facility or a unit in a facility, configured to perform the one or more chemical reactions used in the conversion of carbon monoxide and hydrogen into liquid hydrocarbons.

As briefly described above, the present disclosure provides a gas to liquids (GTL) process that integrates the carbon capture process of at least a portion of carbon dioxide generated during the GTL process or from any other flue gas stream in a conventional hydrocarbon cracking facility. In another aspect, the inventive GTL process utilizes at least a portion of the captured carbon dioxide to reform natural gas for the production of hydrocarbon liquids, such as, for example, Fischer-Tropsch liquids. It should be understood that the operating conditions appropriate for carrying out the inventive GTL process could be readily determined by one of skill in the art in possession of this disclosure.

In one aspect, the inventive GTL process can reduce and/or eliminate the amount of off-gassing of carbon dioxide to the atmosphere. In yet another aspect, the inventive GTL process can reduce and/or eliminate the need to capture and sequester carbon dioxide, for example, in subterranean oil formations. In yet another aspect, all or substantially all of the carbon dioxide produced in the GTL process can be captured and subsequently used in the GTL process. In yet another aspect, no or substantially no carbon dioxide produced in the inventive GTL process is vented to the atmosphere. For example, according to some aspects, the inventive GTL process can reduce the overall carbon footprint relative to that of a conventional process by at least 10%, at least 20%, at least 30%, at least 40%, at least 50%, at least 60%, at least 70%, at least 80%, or even at least 90%. Thus, the inventive GTL process can provide various environmental and/or cost benefits, as compared to conventional GTL processes.

A capture unit, such as, for example, a carbon dioxide capture unit, can, in various aspects, comprise any capture unit, equipment, and/or process suitable for use with the present invention. In one aspect, a capture unit can comprise one or more solvents that can absorb, for example, carbon dioxide. In such a solvent based capture unit, thermal energy, such as, for example, steam, can be used to heat the one or more solvents to remove absorbed carbon dioxide. In other aspects, a capture unit can comprise other equipment and/or configurations, and the present invention is not intended to be limited to any particular capture unit equipment or technology.

In another aspect, all or substantially all of the energy necessary to capture carbon dioxide produced in the process can be provided by the GTL process itself. Thus, in such an aspect, the inventive GTL process can provide improved energy efficiencies over conventional GTL processes.

In yet other aspects, the inventive GTL process can be utilized with existing GTL process equipment, and in various aspects, does not require the addition of new components or control systems.

In various aspects, the inventive GTL process can comprise the introduction of a methane containing feedstock to a reforming unit. In a further aspect, the methane containing feedstock comprises natural gas. In a still further aspect, the methane containing feedstock is derived from natural gas liquids (NGL) and/or dry natural gas. In a yet further aspect, the reforming unit comprises a steam reforming unit. In one aspect, a steam reforming unit can be configured so as to receive a methane containing feedstock and optionally one or more reforming agents. In various aspects, a reforming agent can comprise a hot gas, capable of heating the methane containing feedstock and steam so as to produce syngas. In a specific aspect, the reforming agent can comprise carbon dioxide, such as, for example, is produced by other portions of the process. Prior to introduction of the methane containing feedstock to the reforming unit, the methane containing feedstock can optionally be subjected to a desulfurization step. In a further aspect, the desulfurization step, if performed, can comprise hydrodesulfurization and/or zinc beds. In the reforming unit, the methane containing feedstock can be partially oxidized or reacted with steam and/or carbon dioxide to produce carbon dioxide, carbon monoxide, hydrogen, and water. In a further aspect, the carbon dioxide, carbon monoxide, hydrogen, and water can exist as or be used to produce a syngas. In a still further aspect, the water gas shift reaction can be used to convert a portion of the carbon monoxide to hydrogen. In a yet further aspect, the water gas shift reaction can be used to adjust the hydrogen to carbon monoxide ratio of the syngas to a desired value as needed for FT synthesis operation.

In a further aspect, the resulting syngas can then be converted to one or more desirable hydrocarbon liquids, such as, for example, propylene, butylene, and/or liquids useful in the production of propylene, butylene, and/or products made therefrom. In a still further aspect, the syngas can be introduced to a Fischer-Tropsch synthesis unit configured to receive syngas. In an optional aspect, all or a portion of the syngas can comprise syngas provided from outside the GTL facility or system, for example, from an underground coal gasification (UCG) facility or system. In a yet further aspect, the Fischer-Tropsch synthesis unit can be configured to provide a cracker feed comprising one or more liquid hydrocarbons and thermal energy.

In a further aspect, one or more liquid hydrocarbons can be introduced to a hydrocarbon cracking unit configured to receive a cracker feed of one or more liquid hydrocarbons and to provide a desirable hydrocarbon product and a carbon dioxide by-product gas. In another aspect, the cracker feed of one or more liquid hydrocarbons can be provided by the Fischer-Tropsch synthesis unit. In an optional aspect, all or a portion of the cracker feed of one or more liquid hydrocarbons can be provided from outside the GTL facility or system.

In a further aspect, the cracker feed comprises naphtha. In a still further aspect, the cracker feed comprises at least about 50%, at least about 75% or even at least about 90% by volume of naphtha. In a further aspect, the cracker feed is substantially free of impurities.

As described above, the excess carbon dioxide produced in the reforming unit of a conventional GTL process is typically vented to the atmosphere or captured for sequestration. Venting this carbon dioxide to the atmosphere poses environmental concerns, whereas the capture and sequestration of carbon dioxide can be energy and cost intensive.

In the GTL process of the present invention, a carbon capture process can be integrated with the GTL process such that all or any portion of the carbon dioxide produced in the reforming unit can be captured, for example, via a flue gas capture unit utilizing an amine (e.g., alkanolamine). In a further aspect, the captured carbon dioxide can optionally be compressed and returned to the reforming unit. Once returned to the reforming unit, the captured carbon dioxide can be used to produce additional hydrogen and/or syngas for the production of GTL liquids.

In another aspect, carbon dioxide streams can be captured from one or more locations within a system or facility, such as a boiler and/or cracker, and subsequently utilized within the GTL process as described herein.

In another aspect, the thermal energy produced in the production of hydrocarbon liquids, such as, for example, steam, can be used to generate power. In an optional aspect, the thermal energy can be used to power a turbine. In another aspect, the inventive GTL process can optionally comprise the use of low pressure steam produced in the conversion to liquids (e.g., Fischer-Tropsch process) for thermal value, for example, to reboil solvents used in a carbon dioxide capture unit. In yet another aspect, the inventive process can comprise returning all or a portion of the carbon dioxide from a cracker unit to a reformer unit, and utilizing thermal energy, such as, steam, from a FT synthesis unit to produce power and/or in the conversion of liquids, for example, to reboil solvents used in a carbon dioxide capture unit.

In another aspect, GTL processes can produce a variety of liquid products, including naphtha and diesel. Some conventional GTL processes are optimized to produce higher proportions of diesel (e.g., 70:30 diesel:naphtha) for use as fuel products. In one aspect, the inventive GTL process can be adjusted to produce larger proportions of fuel products, such as diesel, or of chemical value products, such as, naphtha. By customizing the proportion of naphtha produced by the inventive GTL process, a process can be provided such that nearly the whole or substantially whole product output is suitable for cracking into olefins. Thus, in one aspect, the inventive system is customizable to provide a cracker feed comprising one or more predetermined liquid hydrocarbons. In a further aspect, the system can be customized such that the one or more predetermined liquid hydrocarbons can be present in a predetermined concentration. For example, and without limitation, in some aspects a feed stream of naphtha can be produced for an integrated cracker facility such that when used as substitute feedstock in the cracking facility produces an increased percentage of olefins per ton of feed compared to conventional petroleum derived naphtha feeds. Further, in exemplary aspects, at least 5%, at least 10%, at least 15%, or even a higher percentage of olefins per ton of feed compared to a conventional feed can be produced. Thus, it should be appreciated that according to some aspects the inventive GTL process can provide flexibility in producing desirable products based on current market demands and conditions.

In another aspect, the inventive GTL process can reduce dependency on volatile crude oil markets by providing efficient methods to convert natural gas to valuable hydrocarbon liquids, without adverse environmental consequences. In a further aspect, conventional use of gas field products, such as dry gas and NGL, in place of or in addition to petroleum derived naphtha can create imbalances in the product output spectrum from the cracker unit, such as, significant drops in the relative production of propylene and butylenes to ethylene, causing economic losses. In another aspect, the inventive GTL process can provide liquid product streams having higher chemical value than possible using conventional GTL processes. In a yet further aspect, the inventive GTL process can reduce and/or eliminate such imbalances through GTL-cracker integration as utilized within the GTL process as described herein. In an even further aspect, the inventive GTL process can reduce and/or eliminate the imbalances by first processing the same gas feedstock through the GTL process before feeding the gas feedstock as naphtha to the cracker unit.

Thus, in one aspect, the present invention comprises a process wherein carbon dioxide is recycled from a cracking unit to a reforming unit. In another aspect, the present invention provides a process wherein thermal energy, such as, for example, steam, from a FT process is recycled for use in a carbon dioxide capture unit and/or a power unit. In another aspect, the present invention provides a process wherein a hydrocarbon liquid, such as, for example, naphtha, produced in a FT process and/or a cracking unit can be utilized in a cracking unit to improve the output of one or more desirable hydrocarbon products. In yet another aspect, the present invention provides a process wherein hydrogen is recycled from a cracking unit to a FT process (i.e., GTL unit). In yet another aspect, the present invention comprises a process wherein any two or more of the steps described herein are performed. For example, in one aspect, a process can recycle: 1) carbon dioxide from a cracking unit to a reforming unit, and 2) steam from a FT process to a carbon dioxide capture. In another aspect, a process can comprise three steps, for example, wherein 1) carbon dioxide from a cracking unit is returned to a reforming unit, 2) steam from a FT process is returned to a carbon dioxide capture, and 3) hydrogen from a cracking unit is returned to a FT process unit. In other aspects, any one or more of these steps can be performed to the exclusion of any other steps.

In one aspect, the present invention provides a system for producing hydrocarbon compounds, comprising a reforming unit configured to provide a syngas when supplied with a methane containing feedstock; a Fischer-Tropsch synthesis unit configured to receive syngas provided by the reforming unit and configured to provide: i) a cracker feed comprising one or more liquid hydrocarbons, and thermal energy; a hydrocarbon cracking unit, configured to receive the cracker feed of one or more liquid hydrocarbons from the Fischer-Tropsch synthesis unit and to provide a desirable hydrocarbon product and carbon dioxide; and a carbon dioxide capture unit configured to capture at least a portion of the carbon dioxide provided by the hydrocarbon cracking unit; wherein at least a portion of the thermal energy provided by the Fischer-Tropsch synthesis unit is transferred to the carbon dioxide capture unit, and wherein at least a portion of the carbon dioxide by product gas provided by the carbon dioxide capture unit is supplied to the reforming unit as a reforming agent. In another aspect, the hydrocarbon cracking unit can be further configured to provide an output of hydrogen gas and wherein at least a portion of the output hydrogen gas is available for optional hydrogen processing of the cracker feed comprising one or more liquid hydrocarbons.

In another aspect, the present invention provides a method for producing hydrocarbon compounds, comprising a) forming a syngas from the reaction of a methane containing feedstock and a reforming agent; b) subjecting the syngas from step a) to Fischer-Tropsch synthesis conditions effective to provide: i) a cracker feed comprising one or more liquid hydrocarbons, and thermal energy; wherein at least a portion of the thermal energy provided is transferred to a carbon dioxide capture unit; c) subjecting the cracker feed from step b) to hydrocarbon cracking conditions effective to provide a desirable hydrocarbon product and carbon dioxide; and d) capturing at least a portion of the carbon dioxide provided by step c) in the carbon capture unit, wherein at least a portion of the captured carbon dioxide is used as a reforming agent. In yet another aspect, the cracker feed from step b) can be subjected to hydrocarbon cracking conditions effective to provide a desirable hydrocarbon further provides an output of hydrogen gas and wherein at least a portion of the output hydrogen gas is optionally used in hydrogen processing of the cracker feed comprising one or more liquid hydrocarbons.

With respect to FIG. 1, an exemplary GTL process is illustrated, wherein a methane containing feedstock feed 1 and reforming agent 17 are directed to a reforming unit 14 for the production of syngas 16. The syngas 16 can feed a FT synthesis unit 15, wherein hydrocarbon liquids 6, such as, for example, naphtha, are produced in a Fischer-Tropsch process. In an optional aspect, the syngas 16 can comprise syngas 16 provided from outside the GTL facility or system. The hydrocarbon liquids 6 can then be directed to a hydrocarbon cracker unit 13, configured to produce a desirable hydrocarbon product 18 and carbon dioxide 2. Carbon dioxide 2 generated in the hydrocarbon cracker unit 13 can be directed to a carbon dioxide capture unit 11, and optionally ultimately to the reforming unit 14. In an optional aspect, the hydrocarbon liquids 6 can comprise hydrocarbon liquids 6 provided from outside the GTL facility or system. Hydrogen 7, produced in the hydrocarbon cracker unit 13 can be returned to the FT synthesis unit 15, to be utilized in the further processing of hydrocarbon liquids to marketable products. In addition, thermal energy 3, for example, steam, produced in the FT synthesis unit 15 and/or reforming unit 14, can be directed to the carbon dioxide capture unit 11, for example, to reboil or refresh solvents used in the capture of carbon dioxide and/or the optional power unit 9, for example, for thermal value.

Figure 2:
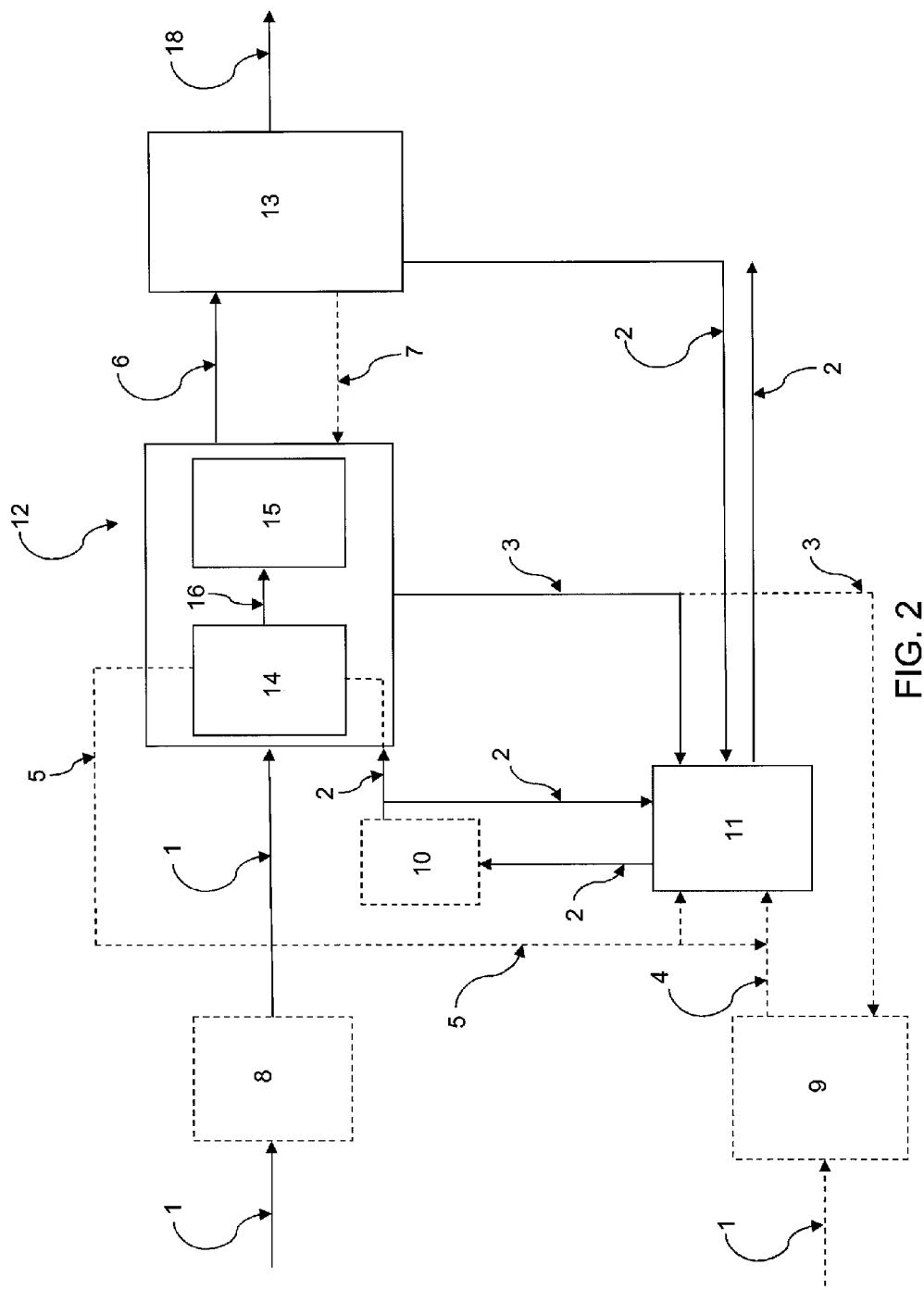
FIG. 2 is an exemplary schematic of an inventive integrated gas to liquids (GTL) process and carbon capture process in accordance with various aspects of the present disclosure.

With respect to FIG. 2, an exemplary GTL process is illustrated, wherein a methane containing feedstock feed 1, is directed to an optional sulfur capture unit 8 and optional power unit 9. The methane containing feedstock feed 1 is then directed to a GTL process unit 12, comprising a reforming unit 14 and a Fischer-Tropsch synthesis unit 15, for the production of syngas 16 and hydrocarbon liquids 6, such as, for example, naphtha, respectively. After processing in the reforming unit 14, the resulting syngas 16 feeds a FT synthesis unit 15, wherein hydrocarbon liquids 6, are produced in a Fischer-Tropsch process. The hydrocarbon liquids 6 can then be directed to a hydrocarbon cracker unit 13 configured to produce a desirable hydrocarbon product 18 and carbon dioxide 2. Hydrogen 7, produced in the hydrocarbon cracker unit 13 can be returned to the GTL process unit 12, to be utilized in the further processing of hydrocarbon liquids to marketable products. Carbon dioxide 2, produced in the hydrocarbon cracker unit 13 can be directed to a carbon dioxide capture unit 11. Flue gas 5 from the reforming unit 14 of the GTL process unit 12, typically comprising substantial quantities of carbon dioxide can be directed from the reforming unit 14 to a carbon dioxide capture unit 11. The flue gas 5 containing carbon dioxide can optionally be mixed with a gas stream 4 from the optional power unit 9, prior to the carbon dioxide capture unit 11. The captured carbon dioxide 2 can be optionally directed to a compression unit 10 and then returned to the GTL process unit 12, where, for example, it can be directed to the reforming unit 14 for the continued processing of natural gas to hydrocarbon liquids. In addition, thermal energy 3, for example, steam, produced in the FT synthesis unit 15 and/or reforming unit 14 of the GTL process unit 12, can be directed to the optional power unit 9, for example, for thermal value, and/or the carbon dioxide capture unit 11, for example, to reboil or refresh solvents used in the capture of carbon dioxide.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A system for producing hydrocarbon compounds, comprising
   a) a reforming unit configured to provide a syngas when supplied with a methane containing feedstock;
   b) a Fischer-Tropsch synthesis unit configured to receive syngas provided by the reforming unit and configured to provide: i) a cracker feed comprising one or more liquid hydrocarbons, and ii) thermal energy;
   c) a hydrocarbon cracking unit, configured to receive the cracker feed of one or more liquid hydrocarbons from the Fischer-Tropsch synthesis unit and to provide a desirable hydrocarbon product and carbon dioxide; and
   d) a carbon dioxide capture unit configured to capture at least a portion of the carbon dioxide provided by the hydrocarbon cracking unit;
   wherein at least a portion of the thermal energy provided by the Fischer-Tropsch synthesis unit is transferred to the carbon dioxide capture unit, and wherein at least a portion of the carbon dioxide by product gas provided by the carbon dioxide capture unit is supplied to the reforming unit as a reforming agent.

2. The system of claim 1, wherein the methane containing feedstock is derived from dry natural gas.

3. The system of claim 1, wherein the methane containing feedstock is derived from natural gas liquids.

4. The system of claim 1, wherein the Fischer-Tropsch synthesis unit is configured to provide a cracker feed comprising naphtha.

5. The system of claim 1, wherein the Fischer-Tropsch synthesis unit is configured to provide the thermal energy in the form of steam.

6. The system of claim 1, wherein the reforming unit is further configured to provide a flue gas comprising carbon dioxide, and wherein the carbon dioxide capture unit is further configured to capture at least a portion of the carbon dioxide in the reformer flue gas.

7. The system of claim 1, wherein the reforming unit is further configured to provide thermal energy and wherein at least a portion of the thermal energy provided by the reforming unit is transferred to the carbon dioxide capture unit, a power unit, or a combination thereof.

8. The system of claim 1, wherein the hydrocarbon cracking unit is further configured to provide an output of hydrogen gas and wherein at least a portion of the output hydrogen gas is available for optional hydrogen processing of the cracker feed comprising one or more liquid hydrocarbons.

9. The system of claim 1, wherein at least a second portion of the thermal energy provided by the Fischer-Tropsch synthesis unit is transferred to a carbon dioxide capture unit, a power unit, or a combination thereof.

10. The system of claim 1, wherein the desirable hydrocarbon product comprises propylene.

11. The system of claim 1, wherein the desirable hydrocarbon product comprises butylene.

12. The system of claim 1, wherein the cracker feed is substantially free of impurities.

* * * * *